United States Patent [19]
Koss

[11] Patent Number: 4,988,357
[45] Date of Patent: Jan. 29, 1991

[54] PENIS PROSTHESIS

[75] Inventor: Walter Koss, Geisenheim, Fed. Rep. of Germany

[73] Assignee: Industriestrasse, Geisenheim, Fed. Rep. of Germany

[21] Appl. No.: 211,075

[22] Filed: Jun. 20, 1988

Related U.S. Application Data

[63] Continuation of Ser. No. 836,230, Feb. 28, 1986, abandoned, which is a continuation of Ser. No. 673,440, Nov. 20, 1984, abandoned.

[30] Foreign Application Priority Data

Dec. 8, 1983 [DE] Fed. Rep. of Germany ....... 8335133

[51] Int. Cl.$^5$ .............................................. A61F 2/26
[52] U.S. Cl. ......................................... 623/11; 128/79
[58] Field of Search ..................... 128/79 A; 604/282; 673/10, 11, 16

[56] References Cited

U.S. PATENT DOCUMENTS

| | | | |
|---|---|---|---|
| 2,268,321 | 12/1941 | Flynn | 604/282 |
| 3,987,789 | 10/1976 | Timm et al. | 128/79 A |
| 4,151,841 | 5/1979 | Barrington | 128/79 A |
| 4,345,339 | 8/1982 | Muller et al. | 623/11 |
| 4,411,260 | 10/1983 | Koss | 128/79 A |
| 4,483,023 | 11/1984 | Hoffman, Jr. et al. | 623/13 |

Primary Examiner—David J. Isabella
Attorney, Agent, or Firm—Gifford, Groh, Sprinkle, Patmore and Anderson

[57] ABSTRACT

A penis prosthesis comprises an implantable flexible rod member formed by a core portion comprising a plurality of wires and an outer casing comprising implantable plastic material around the core portion. At least a part of the wires is individually provided with a casing of elastic plastic material, to provide an enhanced safeguard against injury in consequence of breakage of the wires.

15 Claims, 3 Drawing Sheets

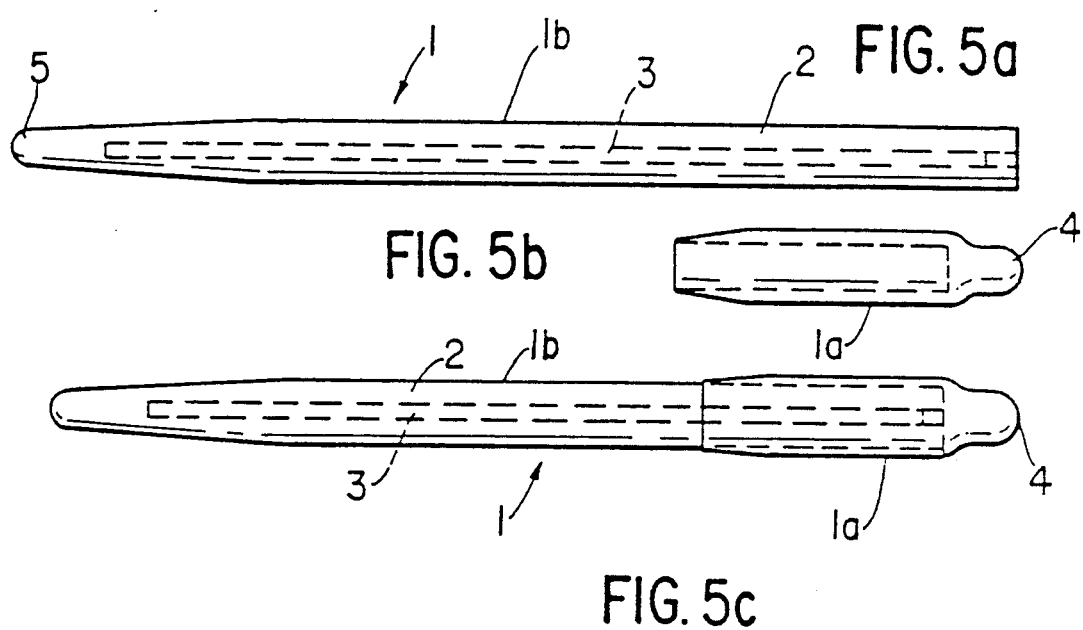

PENIS PROSTHESIS

This is a continuation of co-pending application Ser. No. 836,230 filed on Feb. 28, 1986, now abandoned which is a continuation of application Ser. No. 673,440 filed on Nov. 20, 1984, now abandoned.

BACKGROUND OF THE INVENTION

The invention relates generally to a penis prosthesis and more particularly a penis prosthesis in the form of an implantable flexible rod member.

Penis prostheses are known, comprising an implantable flexible rod which consists of a core portion formed by a plurality of wires, with an outer casing comprising implantable plastic material. Penis prostheses of that construction are disclosed for example in German patent specification No. 2 646 323 or German design No. 78 05 284, and may be used for example for treating impotence in cases involving neurological illnesses, vascular illnesses, injuries and in other situations, being implanted in pairs into the respective erectile or corpora cavernosa of the penis. The penis can then be bent into the respectively required shape and position.

The known prostheses of the above-indicated kind have been found to be successful in many situations, more specifically in a prosthesis construction wherein the wires that make up the core portion comprise high-purity silver. Even after a very large number of bending or flexing movements, such silver wires do not suffer from hardening so that there are virtually no resilient return forces and the penis remains in the bent configuration in which it has been respectively set.

Bending tests on penis prosthesis of the above-indicated kind, having a core portion comprising silver wires, have shown that wire breakages are to be expected only when a very large number of double bends have been made, even when the radii of bending are extremely small and the angles through which the wires are bent are large. Even when further bending is carried out, ends of the wires do not stick out of the prosthesis. Although implanted prosthesis are not subjected to such loadings under practical situations of use, because the radii of bending involved are not so tight and because the prosthesis is not always bent at the same point, nonetheless for reasons of extreme care and precaution, efforts are made further to improve prostheses of the above-indicated kind, in order to provide for further enhanced bending strength.

SUMMARY OF THE INVENTION

An object of the present invention is therefore to provide an implantable penis prosthesis in the form of a flexible rod member having a core portion comprising a plurality of wires, such that the wires do not suffer from breakage even when an extremely large number of bending operations are performed.

Another object of the present invention is to provide a penis prosthesis comprising a core portion formed by an assembly of wires, wherein the wires enjoy enhanced surface protection.

Still another object of the present invention is to provide a penis prosthesis in the form of an implantable flexible rod member having a plurality of wires constituting a core portion, wherein the bending performance of the prosthesis is hardly affected by breakage of a number of the wires making up the core portion.

These and other objects are achieved by a penis prosthesis in the form of an implantable flexible rod member comprising a core portion formed by a plurality of wires and an outer casing comprising implantable plastics material. At least a portion of the wires constituting the core portion is individually provided with a casing of elastic plastic material In such a construction, the wires which preferably comprise high-purity silver are not in direct contact with each other, but rather the plastic-encased wires bear against each other by way of smooth surfaces, thereby permitting sliding movement of the encased wires relative to each other. Tests involving bending of the penis prosthesis of the construction in accordance with the invention have shown that more than a million double bending operations can be carried out, without adversely affecting the proper function and construction of the penis prosthesis.

In an advantageous embodiment, the casing of plastic material on the respective wires is made from a shrink tube. However, the casing may also be formed by casting plastic material around the metal wire, pressing plastic material around the metal wire, or by dipping the metal wire in plastic material. The casing may also be produced by an extrusion operation.

The individual encasing on the respective wires of the penis prosthesis, besides providing same with a substantially higher degree of bending strength, also provide surface protection for the wires. Thus, when using silver wires, black colouration of the surface of the wires has been found to occur from time to time, if the prostheses come into contact with iodine or iodine-bearing vapours. In that case, the iodine may diffuse through the outer casing which generally comprises silicone, thereby giving rise to the black colouration. Encasing the individual wires in the casing of plastic material, in accordance with the invention, which thus seals off the wires, being for example a shrink tube of PTFE, prevents iodine from diffusing through the casing to the wires and thus at least retards and preferably prevents colouration of the wires.

The encased wires are advantageously stranded or twisted together to form the core portion. That construction may involve using a plurality of individual portions of an encased wire, but an advantageous embodiment of the present invention provides the possibility of the core portion comprising preferably a single portion of an encased wire which, by multiple folding at substantially equal spacings, is formed into a plurality of parallel strands which are twisted together. The loops or curved portions of wire which are formed by the folding operations, at the two ends of the bundle of wire strands formed thereby, enhance embedding of the wires into the outer casing.

Another embodiment of the invention provides for using a lattice comprising encased wires which cross each other in substantially perpendicular relationship to make up the core portion, the lattice being rolled together at an inclined angle with respect to the wires.

The core portion itself may be provided with an encasing means comprising a shrink tube before being embedded into the outer casing which advantageously comprises high-quality silicone which is a suitable material for implantation operations. A construction of particular advantage is a double-layer configuration comprising a shrink tube of comparatively low flow temperature, and, over same, a further shrink tube of higher flow temperature. During the shrink operation, the inner shrink tube can then penetrate into the gaps and angles between the encased wires and is firmly pressed into position when the outer tube is subjected to the shrink operation. Instead of two separate shrink tubes, it is also possible in that arrangement to use a double-layer material wherein the inner layer begins to flow at a lower temperature than the outer layer. The inner shrink tube or the inner layer may comprise for example FEP while the outer shrink tube or outer layer may comprise PTFE. It would also be possible to use other fluorine-bearing polymers, for example ETFE, PCTEF, ECTEF and others. The crystallite melting temperature of FEP for example is about 300° C. while that of PTFE is about 350° C.

In order to simplify matching the penis prosthesis to the respective anatomical parameters of the patient both in regard to thickness and in particular length of the prosthesis, and at the same time to avoid the necessity to store substantial quantities of different prostheses, which gives rise to increased expenditure, it may be provided that the rod member is subdivided into at least two portions. In that construction, at the location at which the first and second portions are joined together, one portion has a tubular extension portion which can be pushed over the other portion of the rod member. With such a construction, the penis prosthesis may be adapted to the required length for the patient, by cutting the rod member portions to the appropriate dimension.

Further objects, features and advantages of the present invention will be apparent from the following description of a preferred embodiment thereof.

BRIEF DESCRIPTION OF THE DRAWING

FIG. 5 is a side view of another preferred embodiment of the penis prosthesis in accordance with the teachings of the present invention.

DESCRIPTION OF THE PREFERRED EMBODIMENT

Figure 1:
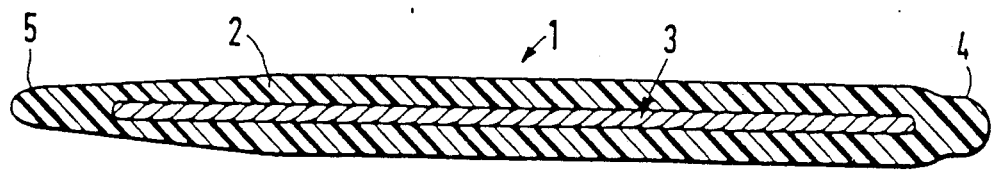
FIG. 1 is a diagrammatic view of an embodiment of a penis prosthesis in accordance with the teachings of the present invention.

Referring therefore now to the drawing, shown therein is a penis prosthesis in the form of an implantable flexible rod member 1 which has an outer casing 2 comprising an implantable plastic material, for example silicone, or another elastomer, and a core portion 3 which is embedded in the outer casing 2. The end of the penis prosthesis which is the distal end after the implantation operation is formed by a soft tip 4 while the other proximal end 5 is formed by a tapering or slender terminal portion.

Figure 2:
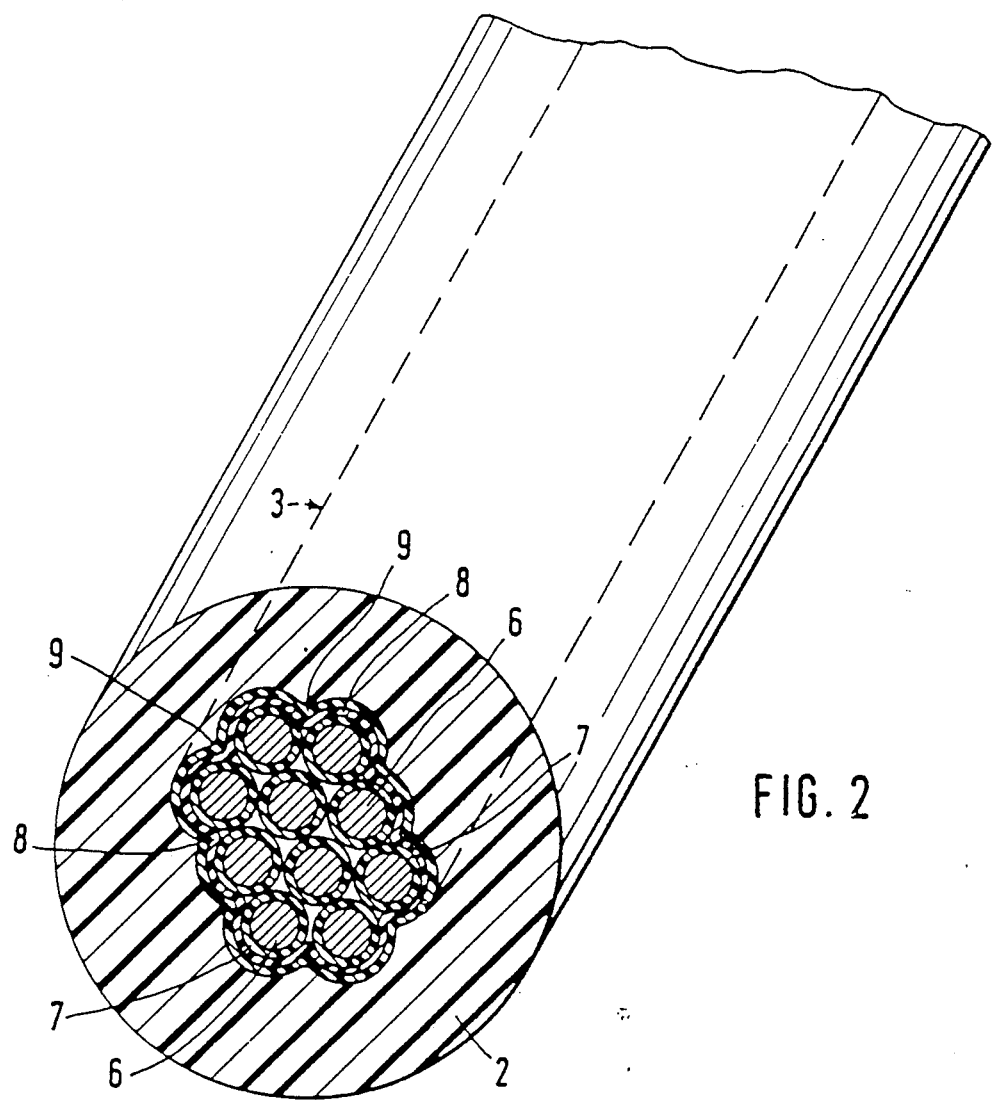
FIG. 2 is a perspective sectional view on an enlarged scale of the embodiment illustrated in FIG. 1.

As can be seen in greater detail from the view illustrated in FIG. 2, the core portion 3 comprises a plurality of wires 6 which comprise a suitable material such as high-purity silver. Each individual wire is encased by a casing 7 of elastic plastic material, being for example in the form of a shrink tube 7 comprising PTFE which is shrunk on to the respective wire 6. The shrink tube 7 initially has an inside diameter of 0.8 mm. The wire 6 with the shrink tube 7 shrink-fitted thereon then has an overall diameter of about 0.85.

Figure 3:
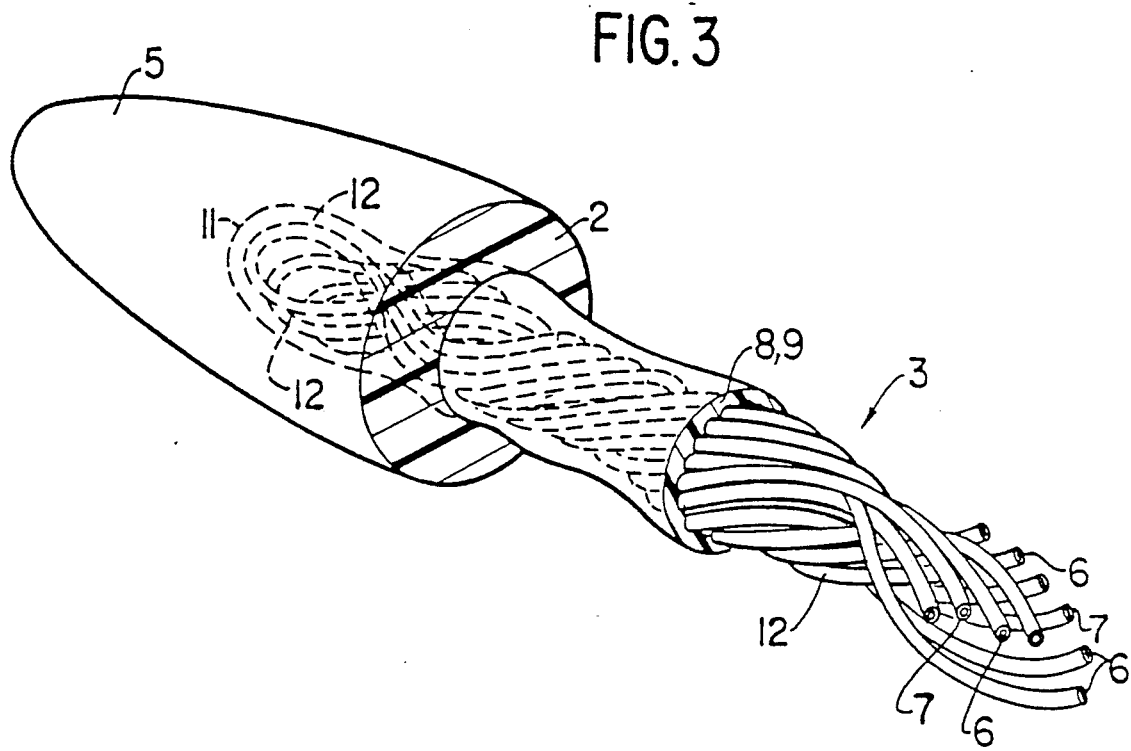
FIG. 3 is a partially exploded perspective view on an enlarged scale of the embodiment illustrated in FIG. 1.

For the purposes of forming the core portion 3, a length of wire 6 with its casing 7, being of a length about ten times the required length of the core portion 3, was folded over at uniform spacings at nine locations 11 along the length of the wire, thereby forming ten wire strands 12 which extend in side-by-side relationship, as shown in FIG. 2 and 3. The wires are twisted or stranded together to ensure that the strands 12 are held together. The bend portions or loops 11 which are formed at the ends of the wire strands 12 forming the core portion 3, by virtue of the bending operation, improve and facilitate embedding the core portion 3 into the outer casing 2.

Before being fitted with the outer casing 2, the encased wires 6, 7 are pushed into two shrink tubes 8 and 9 which are disposed in coaxial arrangement one within the other, the inner tube 8 comprising a material such as FEP and being of an inside diameter of about 4.5 mm in the non-shrunk condition. The outer tube 9 is a thin-walled shrink tube comprising a suitable material such as PTFE. Heat is then applied carefully to perform a shrink operation, the inner tube 8 being heated to such a degree that it begins to flow and thus penetrates into the spaces and angles between the encased wire portions 6, 7 and is firmly pressed into position therein by the outer shrink tube 9. For that purpose, the temperature at which the inner shrink tube 8 begins to flow is lower than the temperature at which the outer shrink tube 9 begins to flow.

In a modification of the above-described specific construction comprising the two shrink tubes 8 and 9, the enclosure means 8 and 9 may be formed by a double-layer material comprising an inner layer 8 and an outer layer 9, the material of the inner layer 8 beginning to flow at a lower temperature than the outer layer 9, thereby to provide the enclosing construction shown in FIG. 2.

Figure 4:
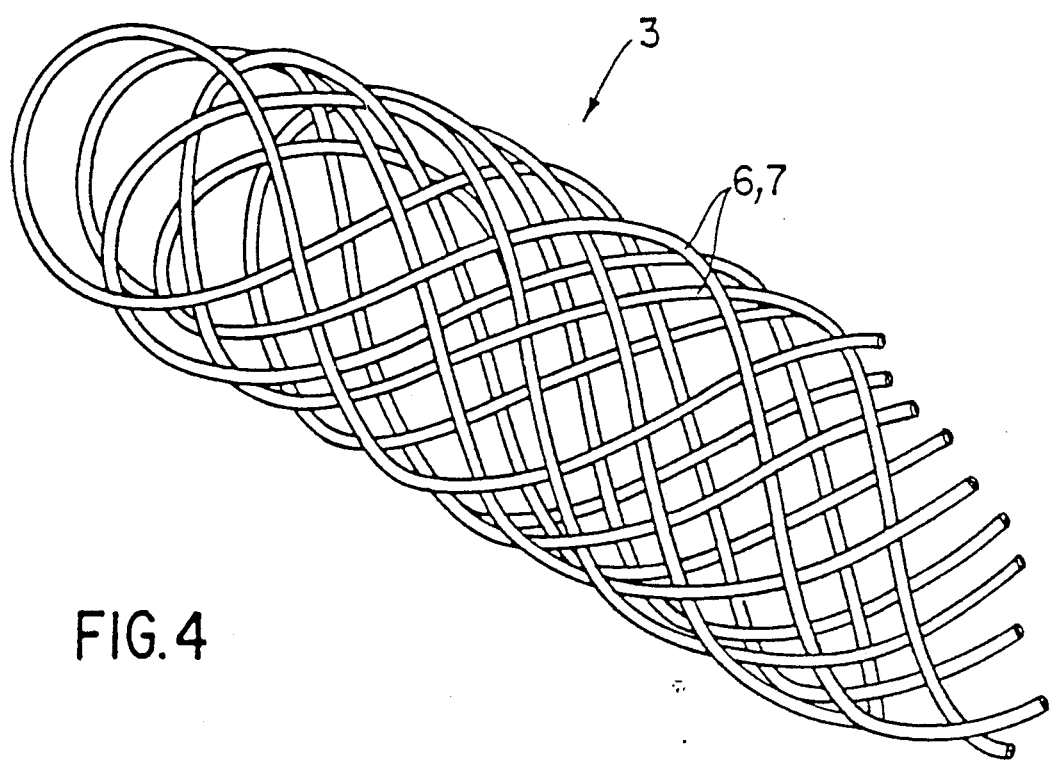
FIG. 4 is a partially exploded perspective view similar to FIG. 3, but with parts removed for clarity, of another preferred embodiment of the penis prosthesis in accordance with the teachings of the present invention.

The encased wires 6, 7 may also be formed by rolling up a lattice or grid of mutually substantially perpendicularly crossing encased wires, with the direction of rolling of the lattice or grid being at an inclination with respect to the directions in which the encased wires 6, 7 extend, thereby to form the core portion 3 as illustrated in FIG. 4.

As shown in FIg. 5, the rod member 1 can be divided into at least two portions 1a and 1b. The portions 1a and 1b are shown in FIGS. 5a and 5b, respectively, and can be fitted together as disclosed in FIG. 5c.

The finished prosthesis 1 has an excellent bending behaviour. It will remain in any position in which it is set by bending, virtually without any resilient return movement long-term bending tests, involving bending the prosthesis through a radius of about 25 mm and with a double bending angle of 2×90°, at a frequency of ninety double bends per minute, were stopped after a million and in some cases one and a half million double bend operations. After than procedure, the prosthesis could still be satisfactorily bent in the long-term bending region, and remained in the respective position in which they were set by bending. Even if individual or all metal wires 6 suffer fracture in such bending tests, the mode of operation of the prosthesis is not detrimentally affected As the wires 6 with their shrink tube casing 7 are fixedly shrunk in and pressed together radially and axially by the shrink tubes or layers 8 and 9, the bending performance of the prosthesis is hardly affected at all, as indicated above, even after one or more wires suffers fracture. The prosthesis reliably prevents wires 6 from sticking out therefrom, which could give rise to a corresponding risk of injury. The wires are protected from foreign substances or bodies from penetrating thereto, by virtue of the shrunk enclosure both on the individual wires 6 and also on the core portion 3.

It will be appreciated that various modifications and alterations may be in the above-described specific embodiments of the principles of this invention, without thereby departing from the spirit and scope thereof.

What is claimed is:

1. A penis prosthesis in the form of an implantable flexible rod member including: a core portion comprising a plurality of metallic wires; a casing of elastic plastic material individually provided on at least a portion of the wires; and an outer casing comprising implantable plastic material enclosing the wires; wherein said casing individually provided on each of said wires comprises a smooth surface which permits sliding movement of said encased wires relative to one another.

2. A penis prosthesis as set forth in claim 1 wherein the individual casing of elastic plastic material comprises a shrink tube on the respective wire.

3. A penis prosthesis as set forth in claim 1 wherein the wires comprise high-purity silver.

4. A penis prosthesis as set forth in claim 1 wherein the wires with individual casings thereon are stranded together to form the core portion.

5. A penis prosthesis as set forth in claim 1 wherein the wires with individual casings thereon are entwined to form the core portion.

6. A penis prosthesis as set forth in claim 1 wherein the core portion comprises a single wire with said casing of elastic plastic material thereon, the wire, by multiple folding at a plurality of at least substantially equal spacings, being formed into a plurality of parallel strands.

7. A penis prosthesis as set forth in claim 6 wherein said strands are twisted together.

8. A penis prosthesis as set forth in claim 1 wherein said core portion comprises a lattice comprising mutually substantially perpendicularly crossing wires with respective and individual casings thereon, rolled together at an inclined angle with respect to the wires to form said core portion.

9. A penis prosthesis as set forth in claim 1 wherein the core portion is provided with an enclosure means comprising shrink tube means around said encased wires.

10. A penis prosthesis in the form of an implantable flexible rod member including: a core portion comprising a plurality of metallic wires; a casing of elastic plastic material individually provided on at least some of the wires; and an outer casing comprising an implantable plastic material enclosing the wires; wherein said casing individually provided on each of said wires comprises a smooth outer surface which permits sliding movement of said encased wires relative to one another; and wherein the core portion is provided with an enclosure means comprising a first shrink tube around said encased wires and a second shrink tube arranged over the first shrink tube in coaxial relationship therewith, the flow temperature of the second shrink tube being higher than that of the first shrink tube.

11. A penis prosthesis in the form of an implantable flexible rod member including: a core portion comprising a plurality of metallic wires; a casing of elastic plastic material individually provided on at least some of the wires; and an outer casing comprising an implantable plastic material enclosing the wires; wherein said casing individually provided on each of said wires comprises a smooth surface which permits sliding movement of said encased wires relative to one another; and wherein the core portion is provided with an enclosure means comprising a two-layer material around side encased wires comprising a flowable inner layer and a flowable outer layer, the inner layer having a lower flow temperature than the outer layer.

12. A penis prosthesis as set forth in claim 1 wherein the rod member is subdivided into at least two separate but joinable portions.

13. A penis prosthesis in the form of an implantable flexible rod member including: an elongate core portion extending in a longitudinal direction comprising a plurality of metallic wire portions extending in at least substantially mutually parallel relationship substantially in the longitudinal direction of the core portion; on each of said wire portions a casing of elastic plastic material; around the array of wire portions with their respective casings of elastic plastic material, an enclosure means of plastic material; and around the enclosure means an outer casing comprising implantable plastic material; wherein said elastic plastic casing on each of said wires comprises a smooth surface which permits sliding movement of said encased wires relative to one another.

14. A penis prosthesis in the form of an implantable flexible rod including a core comprising a plurality of metal wires and an outer casing of implantable plastic material, wherein at least some of said wires are individually provided with a casing of elastic plastic material having a smooth outer surface.

15. A penis prosthesis in the form of an implantable flexible rod member including: a core portion comprising a plurality of metallic wires; a casing of elastic plastic material individually provided on at least some of the wires; and an outer casing comprising an implantable plastic material enclosing the wires; wherein said casing individually provided on each of said wires comprises a smooth outer surface which permits sliding movement of said encased wires relative to one another; wherein the core portion is provided with an enclosure means comprising shrink tube means around said encased wires; and wherein the elastic plastic material provided on the wires comprises a first shrink tube having a flow temperature lower than the flow temperature of the shrink tube means which comprises the enclosure means.

* * * * *